US010881911B2

(12) United States Patent
Kwon et al.

(10) Patent No.: US 10,881,911 B2
(45) Date of Patent: Jan. 5, 2021

(54) GAIT REHABILITATION CONTROL SYSTEM AND METHOD THEREFOR

(71) Applicant: CUREXO, INC., Seoul (KR)

(72) Inventors: Suncheol Kwon, Seoul (KR); Dongmyung Min, Hwaseong-si (KR); Younghwan Kim, Osan-si (KR)

(73) Assignee: CUREXO, INC., Seoul (KR)

( * ) Notice: Subject to any disclaimer, the term of this patent is extended or adjusted under 35 U.S.C. 154(b) by 171 days.

(21) Appl. No.: 15/573,592

(22) PCT Filed: Oct. 7, 2015

(86) PCT No.: PCT/KR2015/010631
§ 371 (c)(1),
(2) Date: Nov. 13, 2017

(87) PCT Pub. No.: WO2016/125979
PCT Pub. Date: Aug. 11, 2016

(65) Prior Publication Data
US 2018/0104542 A1    Apr. 19, 2018

(30) Foreign Application Priority Data
Feb. 4, 2015    (KR) .................. 10-2015-0017308

(51) Int. Cl.
*A63B 24/00*    (2006.01)
*G16H 20/30*    (2018.01)
(Continued)

(52) U.S. Cl.
CPC ........... *A63B 24/0087* (2013.01); *A61H 1/02* (2013.01); *A61H 1/0262* (2013.01);
(Continued)

(58) Field of Classification Search
CPC . A63B 24/0087; A63B 21/4015; A63B 22/04; A63B 71/0622; A63B 24/0075;
(Continued)

(56) References Cited

U.S. PATENT DOCUMENTS

2008/0234113 A1    9/2008  Einav
2009/0036804 A1*   2/2009  Horst ............... A61H 1/0237
                                                    601/5
(Continued)

FOREIGN PATENT DOCUMENTS

EP          2671559 A1     12/2013
KR    10-2008-0024695       3/2008
(Continued)

OTHER PUBLICATIONS

International Search Report for International Application No. PCT/KR2015/010631, dated Jan. 15, 2016.
(Continued)

*Primary Examiner* — Sundhara M Ganesan
*Assistant Examiner* — Shila Jalalzadeh Abyaneh
(74) *Attorney, Agent, or Firm* — Novick, Kim & Lee, PLLC; Jae Youn Kim; Jihun Kim

(57) ABSTRACT

The gait rehabilitation control system according to the present invention comprises an operation device unit for setting gait training mode of a patient and displaying gait state information of the patient; a gait device unit worn on the patient's feet so as to move along with the gait motion of the patient; and a control unit for driving the gait device unit according to the gait training mode set by the operation device unit, wherein the control unit comprises a gait pattern analysis unit for measuring reaction force between the patient's feet and the gait device unit, and analyzing the gait pattern of the patient with the data of the reaction force.

10 Claims, 8 Drawing Sheets

(51) Int. Cl.
| | | |
|---|---|---|
| *A61B 5/11* | (2006.01) | |
| *G06Q 50/22* | (2018.01) | |
| *A61H 1/02* | (2006.01) | |
| *A63B 21/00* | (2006.01) | |
| *A63B 22/00* | (2006.01) | |
| *A63B 21/005* | (2006.01) | |
| *A63B 22/04* | (2006.01) | |
| *A63B 69/00* | (2006.01) | |
| *A63B 71/00* | (2006.01) | |
| *A63B 71/06* | (2006.01) | |
| *G09B 19/00* | (2006.01) | |

(52) U.S. Cl.
CPC .... *A63B 21/0058* (2013.01); *A63B 21/00178* (2013.01); *A63B 21/00181* (2013.01); *A63B 21/4015* (2015.10); *A63B 21/4034* (2015.10); *A63B 22/0017* (2015.10); *A63B 22/04* (2013.01); *A63B 24/0003* (2013.01); *A63B 24/0075* (2013.01); *A63B 69/0064* (2013.01); *A63B 71/0054* (2013.01); *A63B 71/0622* (2013.01); *G06Q 50/22* (2013.01); *G09B 19/003* (2013.01); *G16H 20/30* (2018.01); *A61B 5/112* (2013.01); *A61H 2201/0173* (2013.01); *A61H 2201/0176* (2013.01); *A61H 2201/0196* (2013.01); *A61H 2201/1215* (2013.01); *A61H 2201/1642* (2013.01); *A61H 2201/1666* (2013.01); *A61H 2201/5007* (2013.01); *A61H 2201/5061* (2013.01); *A61H 2201/5097* (2013.01); *A61H 2203/0406* (2013.01); *A61H 2203/0425* (2013.01); *A61H 2205/10* (2013.01); *A63B 2022/002* (2013.01); *A63B 2024/0012* (2013.01); *A63B 2024/0093* (2013.01); *A63B 2071/0081* (2013.01); *A63B 2220/51* (2013.01); *A63B 2220/54* (2013.01); *A63B 2225/50* (2013.01)

(58) Field of Classification Search
CPC .......... A63B 24/0003; A63B 21/00178; A63B 71/0054; A63B 21/4034; A63B 69/0064; A63B 21/0058; A63B 22/0017; A63B 21/00181; A63B 2220/51; A63B 2225/50; A63B 2024/0012; A63B 2220/54; A63B 2024/0093; A63B 2022/002; A63B 2071/0081; A63B 2022/0094; G16H 20/30; G16H 40/67; G09B 19/003; G06Q 50/22; A61H 1/0262; A61H 1/02; A61H 2203/0425; A61H 2205/10; A61H 2203/0406; A61H 2201/5007; A61H 2201/1666; A61H 2201/1215; A61H 2201/0173; A61H 2201/5061; A61H 2201/1642; A61H 2201/0176; A61H 2201/0196; A61H 2201/5097; A61H 21/00178; A61B 5/112

See application file for complete search history.

(56) References Cited

U.S. PATENT DOCUMENTS

| | | | |
|---|---|---|---|
| 2010/0298102 A1 | 11/2010 | Bosecker et al. | |
| 2011/0071442 A1* | 3/2011 | Park | A61H 1/0262 601/35 |
| 2014/0094345 A1* | 4/2014 | Kim | A63B 21/4009 482/7 |
| 2014/0100491 A1 | 4/2014 | Hu et al. | |

FOREIGN PATENT DOCUMENTS

| | | | |
|---|---|---|---|
| KR | 10-2009-0104261 | | 10/2009 |
| KR | 20120057081 A | * | 6/2012 |
| KR | 10-2012-0071555 | | 7/2012 |
| KR | 10-1221046 | | 2/2013 |
| KR | 10-2013-0056026 | | 5/2013 |
| KR | 20130056026 A | * | 5/2013 |

OTHER PUBLICATIONS

Written Opinion with English Translation for International Application No. PCT/KR2015/010631, dated Jan. 15, 2016.

* cited by examiner ately and control training movements, by measuring reaction force of a patient who gets gait training with the gait rehabilitation robot and analyzing the gait pattern of the patient with the data of the measured reaction force.

GAIT REHABILITATION CONTROL SYSTEM AND METHOD THEREFOR

BACKGROUND OF THE INVENTION

1. Field of the Invention

The present invention relates to control technology for controlling a gait rehabilitation robot. More specifically, the present invention relates to a gait rehabilitation control system and method therefor which can monitor gait training situations accurately and control training movements, by measuring reaction force of a patient who gets gait training with the gait rehabilitation robot and analyzing the gait pattern of the patient with the data of the measured reaction force.

2. Description of the Related Art

In general, walking upright that walks with supporting the weight with two legs, is a basic action and function for maintaining the life as a human being. Therefore, when we have obstacles in walking upright, we not only have limitations of exercise physically, but also have difficulties in daily life and social activities. In the case of the patient who has lost the function of walking upright due to a disease or an accident and gets a rehabilitation treatment, it is required to make the patient lose the weight and walk with speed adjusted according to the state of the patient in rehabilitation treatment from the beginning of the treatment.

For this purpose, as disclosed in Korean Patent number 10-0854511 registered on Aug. 20, 2008, a gait rehabilitation control system, providing gait training with a driving control system including a servo motor, has been suggested.

However, the conventional gait rehabilitation control system has limits in measuring the reaction force and analyzing the gait pattern of the patient. As a result, the conventional system cannot monitor the gait state of the patient in real time or provide gait training which is appropriate for each patient.

SUMMARY OF THE INVENTION

The present invention is suggested to solve aforementioned problems. An object of the present invention is to provide a gait rehabilitation control system and method therefor, which are able to provide gait training to the patient with a microprocessor, a control program, and gait data and analyze the gait pattern of the patient with data of reaction force measured in the progress of gait training.

In addition, another object of the present invention is to provide the system and method which can monitor the gait training state of the patient in real time and regulate the strength of the training, through wireless communication with a mobile terminal, such as wireless tablet and smartphone based on touch screen.

A gait rehabilitation control system according to the present invention includes an operation device unit for setting gait training mode of a patient and displaying gait state information of the patient; a gait device unit worn on the patient's feet so as to move along with the gait motion of the patient; and a control unit for driving the gait device unit according to the gait training mode set by the operation device unit, wherein the control unit comprises a gait pattern analysis unit for measuring reaction force between the patient's feet and the gait device unit, and analyzing the gait pattern of the patient with the data of the reaction force.

In addition, a gait rehabilitation control method according to the present invention includes the steps of (a) inputting information of a patient with an operation device unit; (b) selecting the gait training mode of the patient with the operation device unit; and (c) driving a gait device unit according the selected gait training mode and analyzing the gait pattern of the patient with data of reaction force between the patient's feet and the gait device unit in a gait pattern analysis unit.

DETAILED DESCRIPTION OF THE INVENTION

Hereinafter, a gait rehabilitation control system and method according to an embodiment of the present invention would be explained in detail.

Figure 1:
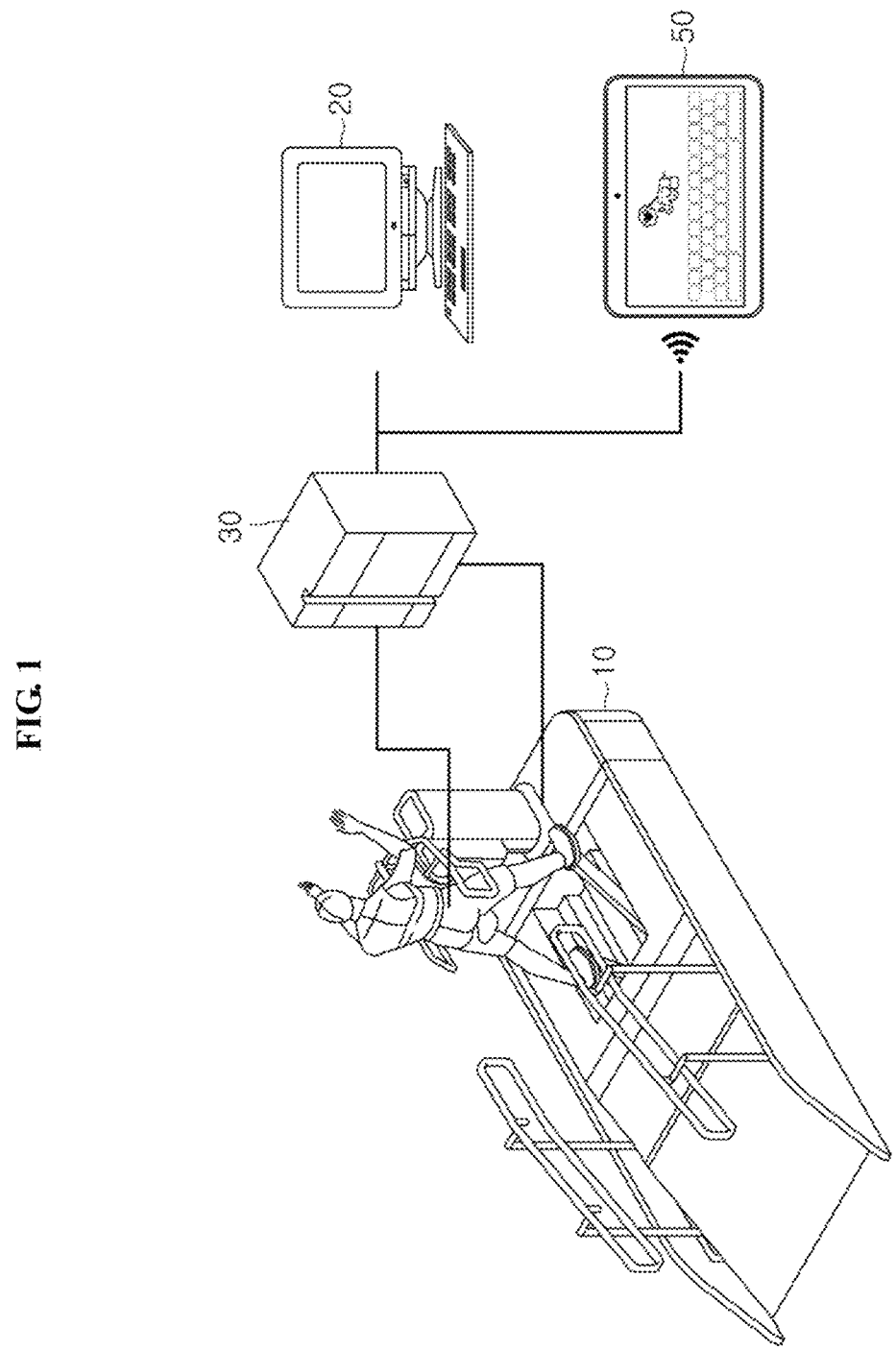
FIG. 1 is a schematic diagram for illustrating the entire configuration of the gait rehabilitation control system according to an embodiment of the present invention.

FIG. 1 is a schematic diagram for illustrating the entire configuration of the gait rehabilitation control system according to an embodiment of the present invention. Referring to FIG. 1, the gait rehabilitation control system comprises a gait device unit 10, an operation device unit 20, a control unit 30, a gait pattern analysis unit 33, and a smart device 50.

The gait device unit 10 is a device that is worn on the patient's feet and moves along with the gait motion of the patient. The patient's feet are put on a foothold, and the patient is moved and seated on a weight support part in shape of saddle. A safety belt is fastened on the patient's chest to fix the upper body of the patient tightly. And the patient's feet on the foothold are fixed tightly with a fixing band. Thus the patient is fixed on the gait device unit 10.

The operation device unit 20 sets gait training mode of the patient and displays gait state information of the patient. The operation device unit 20 according to the present invention sets at least one of the number of steps per minute, step length, step height, foot angle, or gait training mode, which is appropriate for the state of the patient. In addition, the operation device unit 20, in the process of the gait training of the patient, inputs and outputs patient information, sends a report, inputs orders regarding start, stop, emergency stop of the gait training, and sets a threshold value for deciding whether the gait pattern of the patient is normal or not.

Figure 2:
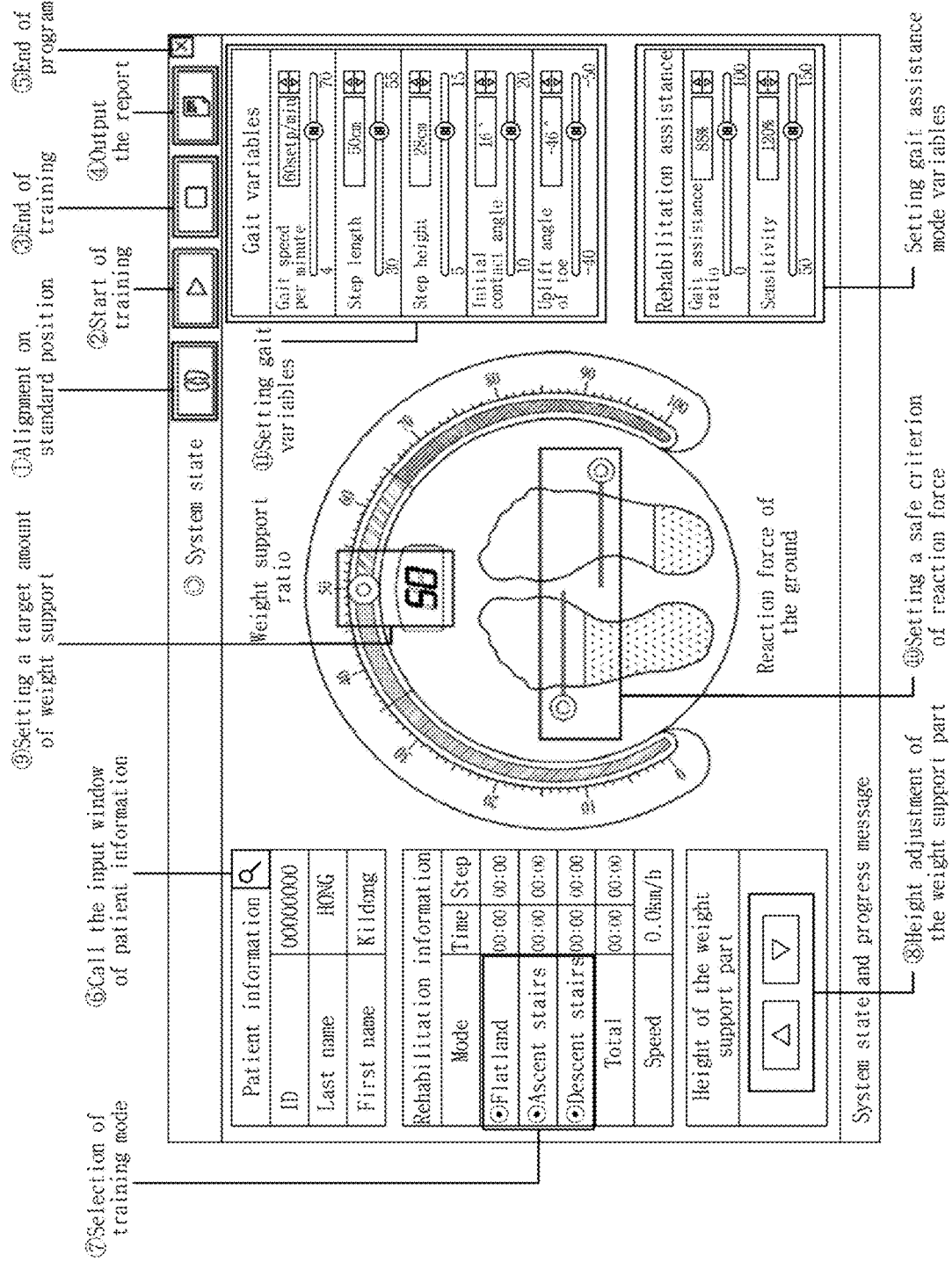
FIG. 2 is a diagram for illustrating an operation device unit of the gait rehabilitation control system according to an embodiment of the present invention.

FIG. 2 is a diagram illustrating an embodiment of the operation device unit 20. Referring to FIG. 2, the operation device unit 20 provides menu. The menu has various submenus such as aligning submenu for aligning the foothold of the gait device unit 10 on standard position, training start submenu, training end submenu, report submenu for outputting the recent training result report of the patient, program end submenu, input window calling submenu for inputting the patient information, such as patient ID of medical institution, first name of the patient, last name of the patient, gender of the patient, height of crotch, height, weight, date of birth, insured part of the patient, extra information. Moreover, the menu also has additional submenus, such as mode selection window submenu for selecting training mode like flatland mode, ascent stairs mode, and descent stairs mode, and weight support height set submenu for adjusting the height of chest/pelvic region support part according to the body type of the patient, weight support target set submenu for setting a target amount of weight support by moving a circular marker left and right, reaction force safe criterion set submenu for setting the standards of the reaction force in preparation for the excessive reaction force, gait variables set submenu for setting variables like gait speed per minute of the patient, gait length, gait height, angle of ankle, and mode variables setting submenu regarding gait assistance like ratio of gait assistance, and sensitivity.

Figure 3:
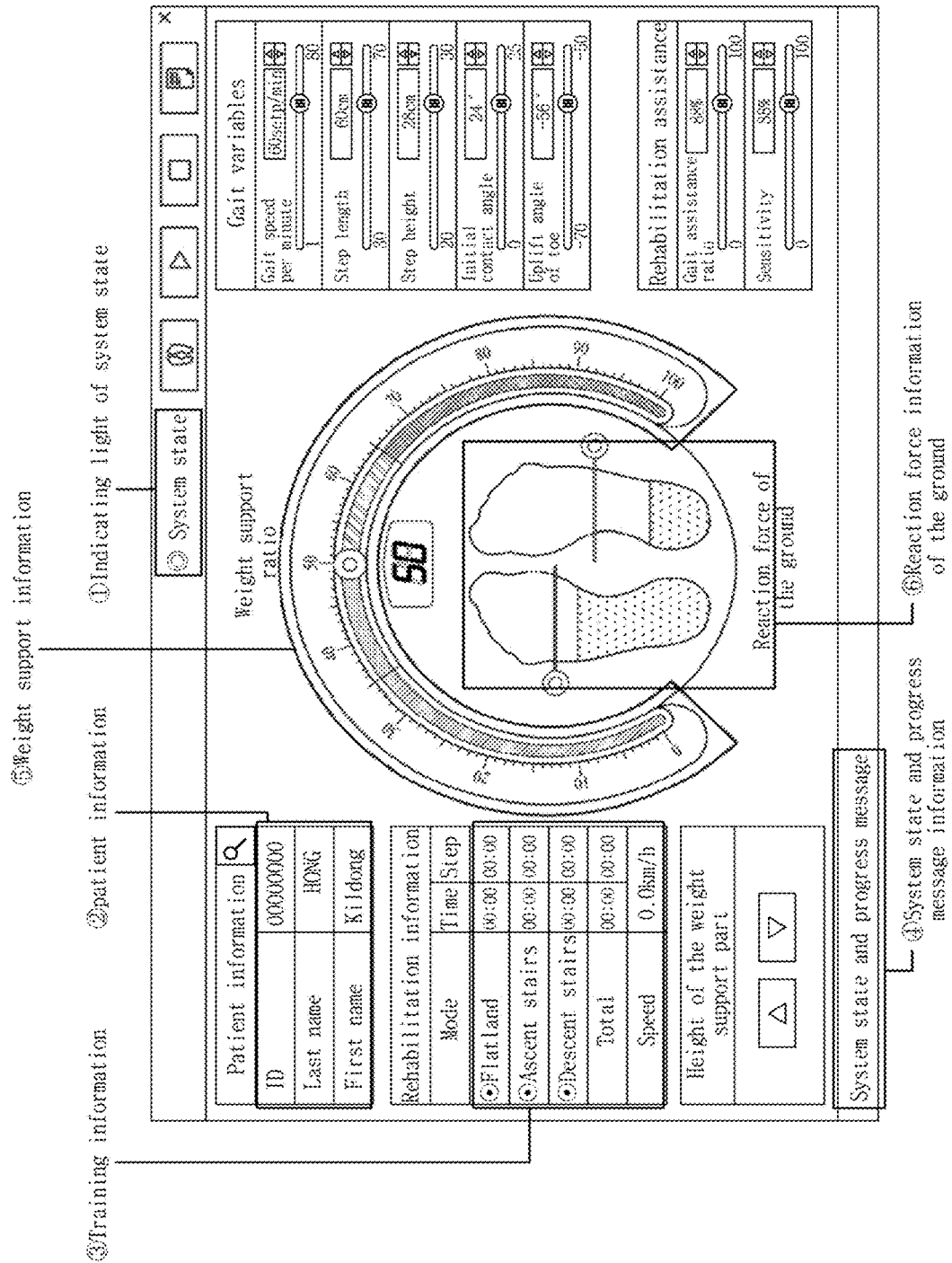
FIG. 3 illustrates an example of monitoring screen displayed on the operation device unit of the gait rehabilitation control system according to an embodiment of the present invention.

FIG. 3 illustrates an example of monitoring screen displayed on the operation device unit 20 of the gait rehabilitation control system according to the present invention.

Referring to FIG. 3, The operation device unit 20 displays an indicating light which indicates the state of the system to check the gait training state, the patient information such as patient ID from the medical institution, name of the patient. And the operation device unit 20 displays training information such as training time for each training mode (flatland, ascent stairs, descent stairs), the number of steps, gait speed per minute, gait speed corresponding to step length, and also displays state information of the system, progress message, information of weight support, and reaction force information of the ground. For reference, the information of weight support, which is about the degree of weight support in progress of the gait training, is displayed in real time as a percentage. And the reaction force information of the ground is displayed as reaction force of the driving unit of the foothold with a reference of the weight of the patient as 200%.

Figure 4:
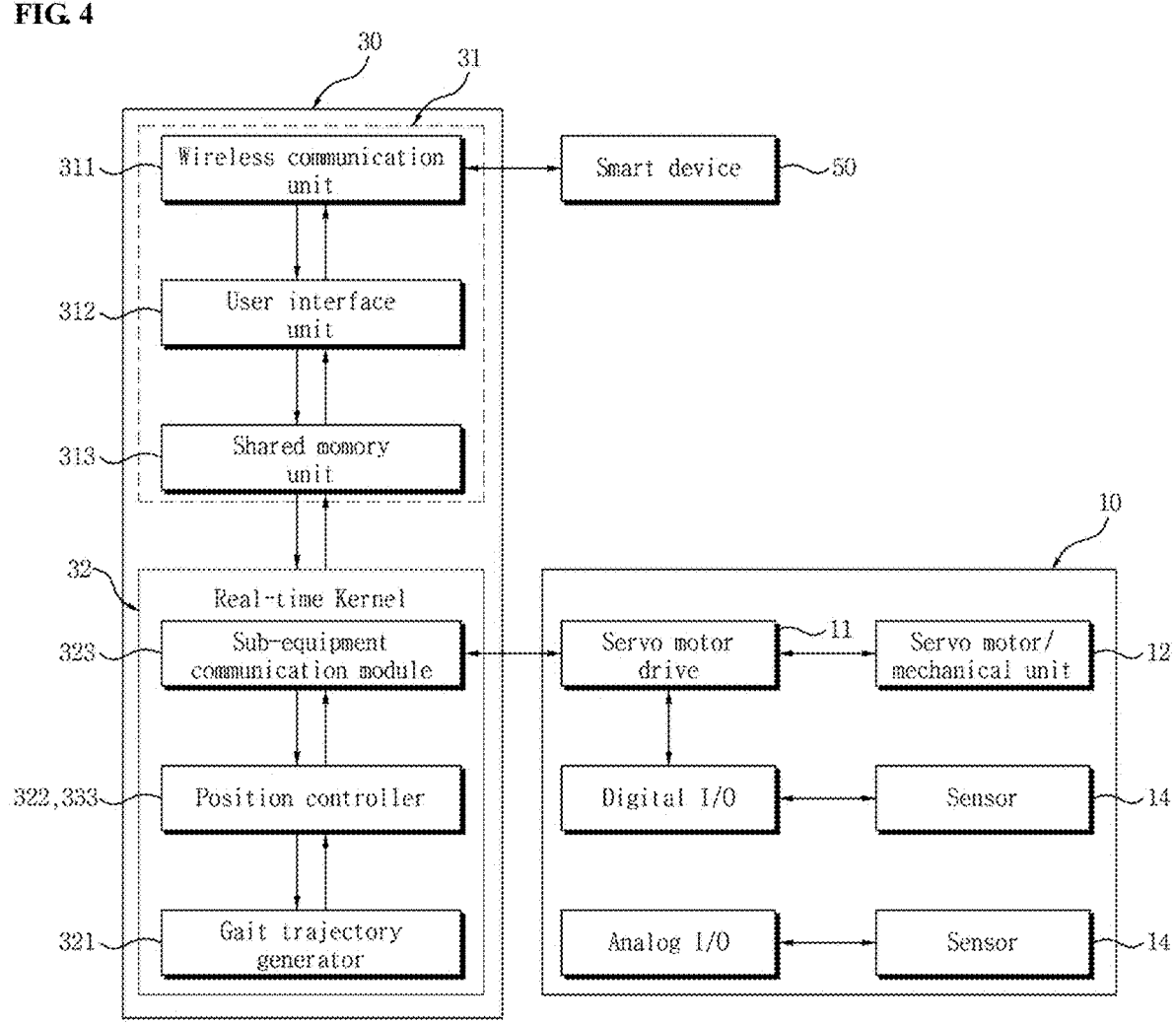
FIG. 4 is a detailed diagram of a control unit of the gait rehabilitation control system according to an embodiment of the present invention.

The control unit 30 drives the gait device unit 10 according to the gait training mode set by the operation device unit 20. As illustrated in FIG. 4, the control unit 30 comprises an operating system kernel 31 and a real-time kernel 32.

The operating system kernel 31 comprises a wireless communication unit 311 for transmitting and receiving the gait training information of the patient with the external smart device 50, a user interface unit 312 which is connected with the wireless communication unit 311 and processes input information from a user according to the gait training of the patient, and a shared memory unit 313 which is connected with the user interface unit 312 and stores set information regarding the gait training of the patient and measured information according to the state of the gait training.

The operating system kernel 31 transmits monitoring information of the state of the gait training and information of functional operation to user interface screen of the operation device unit 20 or the smart device 50. And the operating system kernel 31 transmits the set information regarding the gait training of the patient set with the operation device unit 20 to the real-time kernel 32 through the shared memory unit 313.

The real-time kernel 32 comprises a gait trajectory generator 321, a position controller 322, and a sub-equipment communication module 323.

The gait trajectory generator 321 generates a gait trajectory according to the set gait training mode of the patient. The position controller 322 is connected with the gait trajectory generator 321 and configured to control positions of a servo motor/mechanical unit 12 and include the gait pattern analysis unit 33 for analyzing the gait pattern of the patient. The sub-equipment communication module 323 transmits signal from the position controller 322 to the servo motor/mechanical unit 12 and a sensor 14 and receives signal from the servo motor/mechanical unit 12 and the sensor 14.

The real-time kernel 32 works 500×n (n is a natural number which is equal to or greater than 1) times per second, and calculates the trajectory of gait training every time it works. The position controller 322 calculates the output of the control unit 30 according to the trajectory, and the data of the calculated output is transmitted to a servo motor drive 11 through the sub-equipment communication module 323. The servo motor drive 11 drives the servo motor/mechanical unit 12 based on the data of the calculated output. The sub-equipment communication module 323 receives the sensing data from the sensor 14, and the real-time kernel 32 calculates the trajectory of gait training again.

Figure 5:
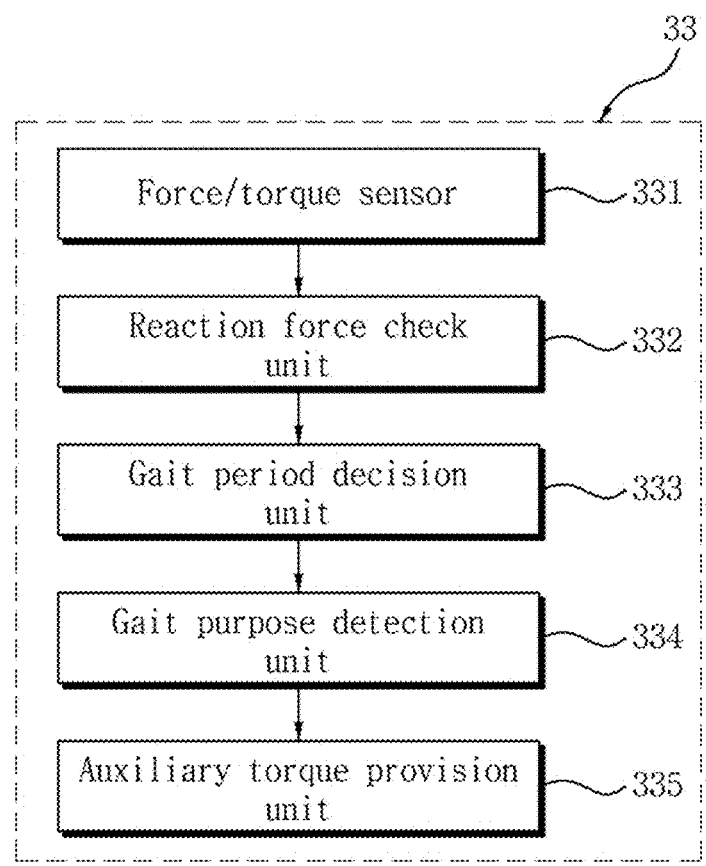
FIG. 5 is a detailed diagram of a gait pattern analysis unit of the gait rehabilitation control system according to an embodiment of the present invention.

The gait pattern analysis unit 33 measures the reaction force between the patient's feet and the gait device unit 10, and analyzes the gait pattern of the patient with the data of the reaction force. As illustrated in FIG. 5, the gait pattern analysis unit 33 according to the present invention comprises a force/torque sensor 331, a reaction force check unit 332, a gait period decision unit 333, a gait purpose detection unit 334, and an auxiliary torque provision unit 335.

The force/torque sensor 331 measures the reaction force between the patient's feet and the gait device unit 10. The reaction force check unit 332 checks whether the measured reaction force is equal to or greater than a threshold value regarding the reaction force of the gait pattern. It is desirable that the reaction force check unit 332 stops the gait device unit 10 from operating when the reaction force is checked to be equal to or greater than the threshold value.

Figure 6:
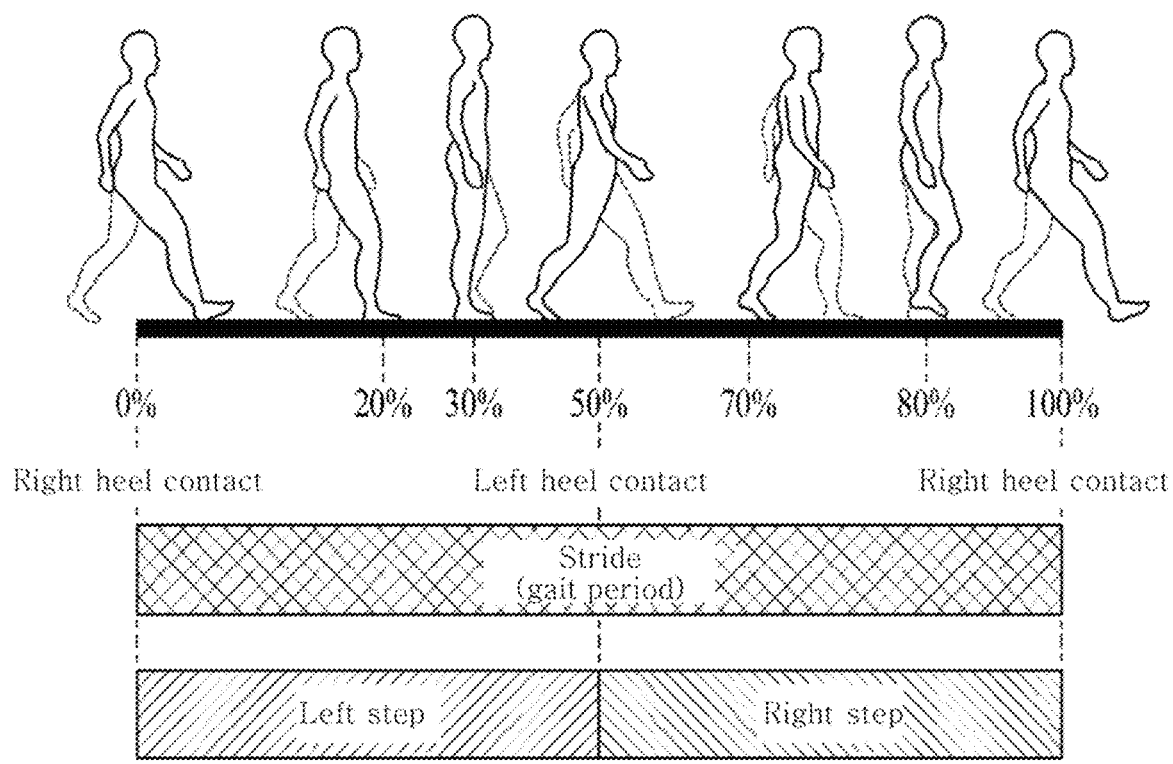
FIG. 6 is a diagram illustrating a concept for calculating a gait period according to an embodiment of the present invention.

In the gait period of the patient illustrated in FIG. 6, the gait period decision unit 333 decides whether the gait of the patient is in stance phase in which feet are contacted with the ground, or swing phase in which feet are stay away from the ground. When it is in the swing phase, the basic operation is controlled to be performed consistently. On the other hand, when it is not in the swing phase, preferably it is checked whether the gait is purposed or not.

The gait purpose detection unit 334 detects the gait purpose of the patient when the weight of the patient is applied, so as to recognize whether the patient is moving his feet by himself.

The auxiliary torque provision unit 335 provides auxiliary gait torque to increase the gait speed when the gait purpose of the patient is detected. With this, the strength of the gait training can be regulated.

The smart device 50 is linked to the medical institution and can monitor the state of the patient and the situation of the gait training in real time through wireless communication with the operation device unit 20. With the smart device 50, the patient can receive information of training from the medical team in long distance, not only by the operation device unit 20 fixed in the system.

The gait rehabilitation control method using the gait rehabilitation control system is described below.

Figure 7:
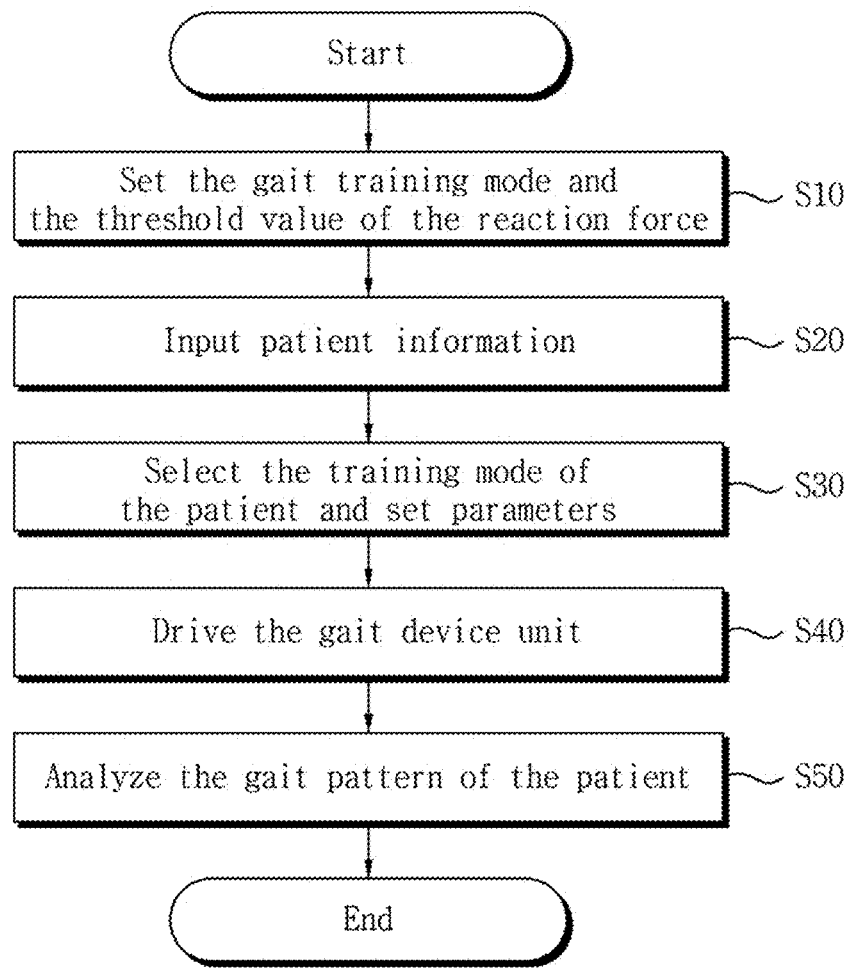
FIG. 7 is a flowchart for illustrating the gait rehabilitation control method according to an embodiment of the present invention.

FIG. 7 is a flowchart for illustrating the gait rehabilitation control method according to the present invention.

In step S10, The threshold value of the reaction force used for the basic gait training mode and the analysis of the gait pattern is set with the operation device unit 20. In an embodiment of the present invention, the basic gait training mode includes flatland mode, ascent stairs mode, and descent stairs mode. The threshold value of the reaction force is set regarding right foot and left foot each.

And then, in step S20, the patient information is inputted with the operation device unit 20. The patient information includes at least one of patient ID of medical institution, first name of the patient, last name of the patient, gender of the patient, height of patient's crotch, height of the patient, weight of the patient, patient birth date, or injured part of the patient.

Next, in step S30, the gait training mode is selected with the operation device unit 20. The operation device unit 20 sets at least one of gait training mode, the number of steps per minute, step length, step height, or foot angle, which is appropriate for the state of the patient.

And then, the control unit 30 drives the gait device unit 10 according to the selected gait training mode in step S40. And in step S50, the gait pattern analysis unit 33 analyzes the gait pattern of the patient with the data of reaction force between the patient's feet and the gait device unit 10.

Figure 8:
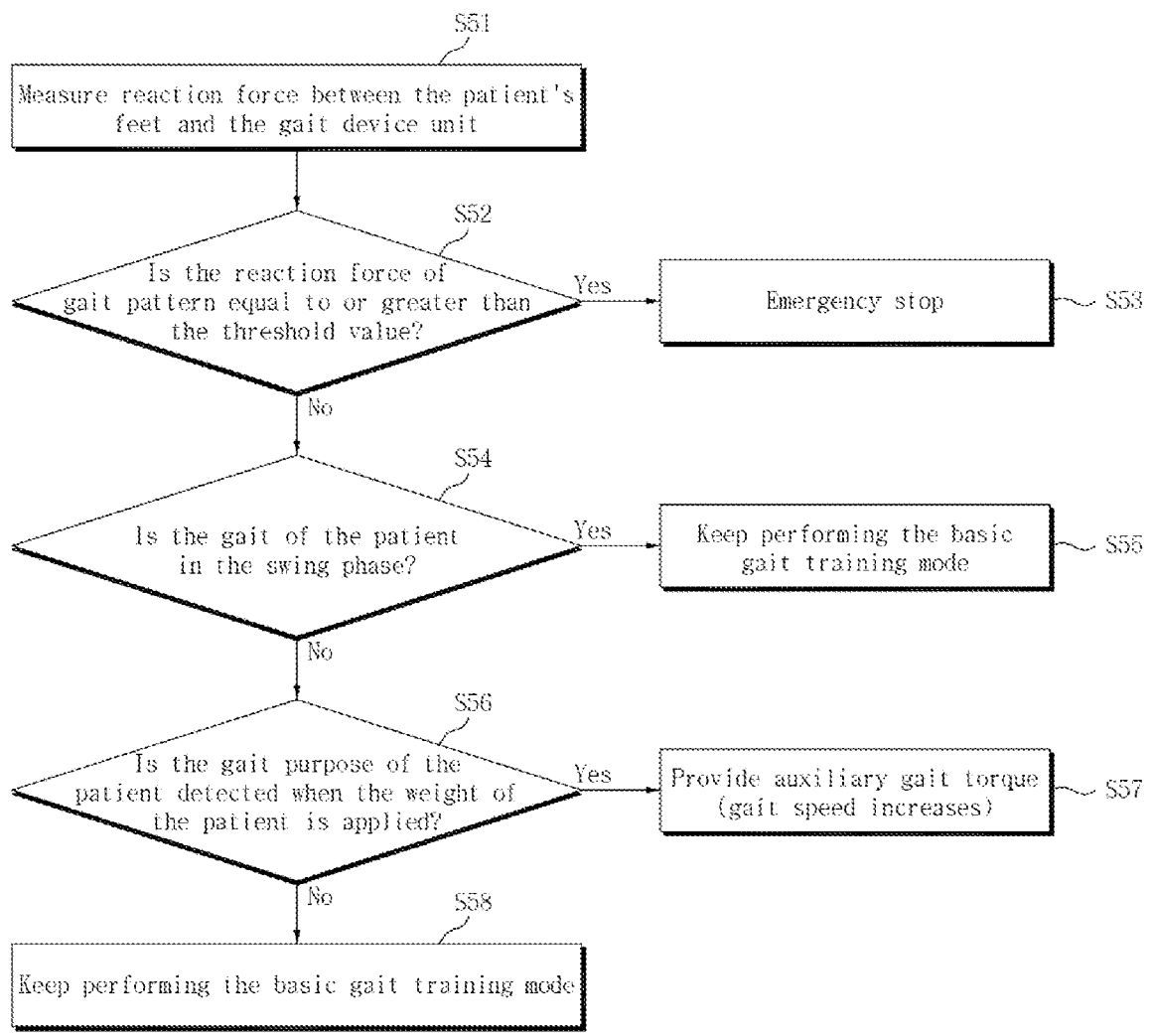
FIG. 8 is a flowchart for illustrating detailed flow in step S50 of the gait rehabilitation control method according to an embodiment of the present invention.

As illustrated in FIG. 8, the step S50 includes steps S51, S52, and S53. That is, the force/torque sensor 331 measures the reaction force between the patient's feet and the gait device unit 10 in the step S51. And in the step S52, the reaction force check unit 332 checks whether the reaction force measured in step S51 is equal to or greater than the threshold value. When the reaction force is checked to be equal to or greater than the threshold value, the gait device unit 10 is stopped as the emergency action in the step S53.

When the reaction force is less than the threshold value in the step S52, the gait period decision unit 332 decides whether the gait of the patient is in stance phase in which feet are contacted with the ground, or swing phase in which feet are stay away from the ground in step S54. When it is decided that the gait of the patient is in the swing phase in the step S54, the selected gait training mode is maintained continuously in step S55.

When it is decided that the gait of the patient is not in the swing phase in the step S54, in step S56, the gait purpose detection unit 334 detects whether the patient is moving his feet by himself when the weight of the patient is applied in the initial stance phase. When it is decided that the patient is moving his feet by himself with the analyzed gait pattern in the step S56, the auxiliary torque provision unit 335 provides auxiliary gait torque to increase gait speed in step S57. On the other hand, when it is decided that the patient is not moving his feet by himself in the step S56, the set basic gait training mode is maintained continuously in step S58.

As mentioned above, the system and method according to the present invention analyze the gait pattern with the data of the reaction force measured in the progress of the gait training. Accordingly, it can make an accurate decision for gait training situations and regulate the strength of gait training based on the gait pattern of the patient, thereby increasing greatly the effect of gait training for each patient.

In addition, it can monitor the gait state of the patient and necessary amount of training in real time and provide the appropriate training for the patient, through wireless communication with mobile terminals which belong to medical team, such as wireless tablets or smart phones based on touch screen.

Moreover, it builds a database regarding gait training contents and the data of the reaction force of the patient to know and manage improvements in gait abilities consistently. Accordingly, the patient can get good results in rehabilitation in a short time.

The above description is suggested only as an exemplary embodiment for realizing the gait rehabilitation control system and method therefor according to the present invention described above. The present invention is not limited to the exemplary embodiment. As a person skill in the art will recognize from the previous detailed description and from the figures and claims, modifications and changes can be made to the preferred embodiments of the invention without departing from the scope of this invention defined in the following claims.

What is claimed is:

1. A gait rehabilitation control system comprising:
an operation terminal configured for selecting a gait training mode of a patient and displaying gait state information of the patient;
a gait device having a foothold configured for receiving the patient's feet so as to move along with a gait motion of the patient; and
a control unit comprising a microprocessor and configured to:
generate a gait trajectory corresponding to the gait training mode selected;
drive the gait device according to the gait trajectory;
measure reaction force between the patient's feet and the gait device;
check whether the measured reaction force is equal to or greater than a threshold value, and stop the gait device when the reaction force is equal to or greater than the threshold value;
determine, when the measured reaction force is less than the threshold value, whether the gait motion of the patient is in a stance phase or a swing phase in the generated gait trajectory;
determine, when the gait motion of the patient is in the stance phase, whether the patient has a gait purpose when a weight of the patient is applied in an initial stance phase of the gait motion of the patient; and
provide an auxiliary gait torque to the gait device so as to increase a gait speed thereof when it is determined that the patient has the gait purpose.

2. The system according to claim 1, wherein the operation terminal further sets at least one of a number of steps per minute, a step length, a step height, or a foot angle.

3. The system according to claim 2, wherein the operation terminal, during gait training of the patient, inputs and outputs patient information, sends a report, and inputs orders regarding a start, a stop, and an emergency stop of the gait training.

4. The system according to claim 1, wherein the control unit further comprises an operating system kernel and a real-time kernel, wherein the operating system kernel is configured to:
transmit and receive gait training information of the patient with an external mobile terminal, process input information from a user regarding the selected gait training mode of the patient, and store set information regarding the gait training of the patient, position measure values of a servo motor and sensing data of a sensor during gait training.

5. The system according to claim 4, wherein the real-time kernel is configured to:

generate the gait trajectory according to the selected gait training mode of the patient, control positions of the servo motor, and transmit a signal to the servo motor and the sensor, and receive another signal from the servo motor and the sensor.

6. The system according to claim 1, further comprising a smart device for checking a gait training state of the patient, and transmitting an input signal to the control unit through wireless communication.

7. A gait rehabilitation control method, comprising the steps of:

(a) inputting information of a patient via an operation terminal;

(b) selecting a gait training mode of the patient via the operation terminal; and (c) generating a gait trajectory corresponding to the selected gait training mode, driving a gait device having a foothold for receiving the patient's feet, according to the gait trajectory, and analyzing, by a control unit comprising a microprocessor, a gait pattern of the patient using data of reaction force between the patient's feet and the gait device, wherein the step (c) comprises the steps of:

(c-1) measuring the reaction force between the patient's feet and the gait device;

(c-2) checking whether the measured reaction force is equal to or greater than a threshold value;

(c-3) stopping the gait device when the reaction force is equal to or greater than the threshold value;

(c-4) determining whether a gait motion of the patient is in a stance phase or a swing phase in the generated gait trajectory when the reaction force is less than the threshold value;

(c-5) determining, when the gait motion of the patient is in the stance phase, whether the patient has a gait purpose when a weight of the patient is applied during an initial stance phase of the gait motion of the patient; and (c-6) providing an auxiliary gait torque to the gait device so as to increase a gait speed thereof when it is determined that the patient has the gait purpose.

8. The method according to claim 7, wherein the step (b) further comprises the step of setting at least one of a number of steps per minute, a step length, a step height, or a foot angle.

9. The method according to claim 7, further comprising the step of:

continuing to perform the selected gait training mode when it is determined that the gait motion of the patient is in the swing phase.

10. The method according to claim 7, prior to the step (a), further comprising the step of (d) setting the threshold value of the reaction force with the operation terminal.

* * * * *